(12) United States Patent
Deckard (10) Patent No.: US 8,556,858 B2
(45) Date of Patent: Oct. 15, 2013

(54) ANCHOR ASSEMBLY

(75) Inventor: Michael D. Deckard, Solsberry, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 676 days.

(21) Appl. No.: 12/170,271

(22) Filed: Jul. 9, 2008

(65) Prior Publication Data

US 2010/0010448 A1    Jan. 14, 2010

(51) Int. Cl.
*A61M 5/32* (2006.01)

(52) U.S. Cl.
USPC .......................................... 604/174; 604/500

(58) Field of Classification Search
USPC ............ 604/104, 164.04, 174, 175, 910, 500, 604/506–517; 606/232
See application file for complete search history.

(56) References Cited

U.S. PATENT DOCUMENTS

| | | | |
|---|---|---|---|
| 5,092,850 A | 3/1992 | Buma et al. | |
| 5,123,914 A * | 6/1992 | Cope | 606/232 |
| 5,374,254 A | 12/1994 | Buma et al. | |
| 5,399,165 A * | 3/1995 | Paul, Jr. | 604/95.04 |
| 5,626,614 A | 5/1997 | Hart et al. | |
| 5,716,347 A | 2/1998 | Gibbs et al. | |
| 5,720,734 A | 2/1998 | Copenhaver et al. | |
| 5,814,071 A | 9/1998 | McDevitt et al. | |
| 5,948,002 A | 9/1999 | Bonutti et al. | |
| 5,954,732 A | 9/1999 | Hart et al. | |
| 6,033,430 A | 3/2000 | Bonutti et al. | |
| 6,059,800 A | 5/2000 | Hart et al. | |
| 6,110,183 A | 8/2000 | Cope et al. | |
| 6,312,448 B1 | 11/2001 | Bonutti et al. | |
| 6,315,789 B1 | 11/2001 | Cragg et al. | |
| 6,402,722 B1 | 6/2002 | Snow et al. | |
| 6,589,208 B2 | 7/2003 | Ewers et al. | |
| 6,592,610 B2 * | 7/2003 | Beyar | 606/232 |
| 6,699,263 B2 | 3/2004 | Cope et al. | |
| 6,706,047 B2 | 3/2004 | Tanner et al. | |
| 7,004,959 B2 | 2/2006 | Bonutti et al. | |
| 2003/0191497 A1 | 10/2003 | Cope et al. | |
| 2004/0116894 A1 | 6/2004 | DeLegge et al. | |
| 2005/0251208 A1 * | 11/2005 | Elmer et al. | 606/232 |
| 2005/0251209 A1 | 11/2005 | Saadat et al. | |
| 2006/0015125 A1 | 1/2006 | Swain et al. | |
| 2006/0030884 A1 | 2/2006 | Yeung et al. | |
| 2006/0241579 A1 | 10/2006 | Kawaura et al. | |
| 2007/0088259 A1 | 4/2007 | Chu et al. | |
| 2007/0106330 A1 | 5/2007 | Rosenberg et al. | |
| 2007/0112385 A1 | 5/2007 | Conlon et al. | |
| 2007/0150002 A1 * | 6/2007 | Szabo et al. | 606/232 |

* cited by examiner

*Primary Examiner* — Kami A Bosworth (74) *Attorney, Agent, or Firm* — Brinks Hofer Gilson & Lione (57) ABSTRACT

An anchor assembly is used with a medical device to engage the medical device against a body wall. The anchor assembly includes a pivotable anchor and a filament. The anchor is seated in a longitudinal orientation within a recessed channel located at the distal end of the medical device. Pulling on a proximal free end of the filament causes the anchor to pivot from a longitudinal orientation to a perpendicular orientation. The anchor in the perpendicular orientation engages against a body wall to immobilize the medical device.

18 Claims, 7 Drawing Sheets

ANCHOR ASSEMBLY

TECHNICAL FIELD

The present invention relates to an anchor assembly for medical devices.

BACKGROUND

Medical practitioners currently use stabilizing elements to immobilize catheters and tubes within various body lumens, including the gastro-intestinal tract and the biliary duct.

One type of known stabilizing device is a drainage catheter used to drain the kidney or biliary system. These catheters have been developed with so-called pigtail loops at their distal ends to prevent accidental removal from the target drainage site. The pigtail loop is tightened by pulling on the proximal end of a filament, which extends within a lumen through the catheter. The distal end of the filament emerges from the lumen, extends along the outer surface of the catheter, and affixes to the distal tip of the catheter. Pulling on the proximal free end of the filament pulls the distal end of the catheter into a pigtail loop. The pigtail loop stabilizes the catheter during drainage of fluid.

Although well-suited for its intended purpose, these pigtail catheters possess numerous drawbacks. For example, the filament may be prone to breakage or degradation (e.g., drainage fluid may solidify and accumulate on the filament) because the wire is typically disposed within the same lumen as the fluid contents that are being drained. Additionally, the distal portion of the filament is not concealed within the lumen. Rather, it is exposed to the drainage environment. As a result, the distal portion of the filament is also prone to breakage or degradation. Damage of the filament may decrease the capability of the filament to pull the distal end of the catheter into the desired pigtail loop configuration, which can result in the release of the distal end of the loop with the possibility that the catheter is withdrawn from the patient.

Sutures are typically connected to the stabilizing element. Pulling on the suture causes the stabilizing element to immobilize the medical device at a target site. However, these sutures are typically disposed outside of the medical device. Thus, the sutures over time may break or degrade due to the inherent acidic environment within the gastro-intestinal tract and the biliary duct. As a result, conventional stabilizing elements may be prone to failure.

Current stabilizing elements also are problematic because they increase the delivery profile of the catheter, thereby making delivery through relatively narrow body lumens problematic. Even if delivery to the target site is possible, conventional stabilizing elements present the additional problem of not possessing adequate holding strength to sufficiently anchor the catheter against a body wall.

Accordingly, there has not been provided an effective anchoring assembly for stabilizing and immobilizing a catheter against a body lumen.

SUMMARY

In a first aspect of the invention, a medical device with an anchor assembly is provided. An elongate member is provided having a proximal end and a distal end. The elongate device comprises a longitudinally oriented first channel disposed in an outer surface near the distal end. A pivotable anchor is removably disposed within the first channel. The pivotable anchor is movable from the first channel to a perpendicular orientation outside the first channel and adjacent to the elongate member. A biocompatible filament has a first attached end affixed to the anchor and a second unattached proximal end disposed outside of a patient, the filament proximally extending from the first attached end to the second unattached end within a lumen of the elongate member. The anchor is configured to pivot from the longitudinal orientation within the first channel to the perpendicular orientation outside the first channel upon application of a tensile force to the second unattached proximal end of the filament. The anchor in the perpendicular orientation is configured to engage against a body wall to inhibit movement of the medical device thereto.

In a second aspect of the invention, a medical device with an anchor assembly is provided. An elongate device has a proximal end and a distal end, the elongate device comprising a longitudinally oriented first channel disposed in an outer surface near the distal end. A pivotable anchor is removably disposed within the first channel. The anchor comprises a first end and a second end, and an effective diameter less than or equal to a depth of the channel. The anchor is movable from the first channel to a perpendicular orientation outside the first channel and adjacent to the elongate member. A first tension member has a first attached end affixed to the anchor. The first attached end is affixed to the anchor at about a midpoint of the anchor. The first tension member further comprises a second unattached proximal end located outside of a patient. The first tension member proximally extends from the first attached end to the second unattached end within a first lumen of the elongate device. A lockable connector is operably connected to the proximal end of the elongate member. The lockable connector comprises a pivotal lever having a cam surface and movable between a locked position and an unlocked position. The cam surface engages the tension member when in the locked position. The anchor is configured to pivot from the longitudinal orientation within the first channel to the perpendicular orientation outside of the first channel upon application of a tensile force to the second unattached proximal end of the tension member. The anchor in the perpendicular orientation is configured to engage against a body wall to inhibit movement of the medical device thereto.

In a third aspect, a method of anchoring an elongate member within a body lumen is provided. An anchor assembly is provided. The assembly comprises an anchor and a biocompatible filament having a first attached end affixed to the anchor and a second unattached proximal end. The anchor is loaded within a channel along an outer surface of the elongate member, wherein the anchor is longitudinally oriented within the channel. The second unattached proximal end is configured to be disposed through a lumen of the elongate member. The second unattached proximal end extends through the lumen of the elongate member and emerges from the lumen as a free end outside of a body of a patient. The elongate member is positioned with the anchor assembly at a target body site. The free end is pulled with a sufficient force so as to pivot the anchor from the longitudinal orientation to a perpendicular orientation relative to the elongate member. The anchor in the perpendicular orientation engages against a body wall of the target body site so as to secure the elongate member thereto.

BRIEF DESCRIPTION OF THE DRAWINGS

Embodiments will now be described by way of example with reference to the accompanying drawings.

FIG. 2B is an expanded view of FIG. 2a.

DETAILED DESCRIPTION

The embodiments are described with reference to the drawings in which like elements are referred to with like numerals. The relationship and functioning of the various elements of the embodiments are better understood by the following detailed description. However, the embodiments as described below are by way of example only, and the invention is not limited to the embodiments illustrated in the drawings. It should also be understood that the drawings are not to scale and in certain instances details have been omitted, which are not necessary for an understanding of the embodiments, such as conventional details of fabrication and assembly.

Figure 1:
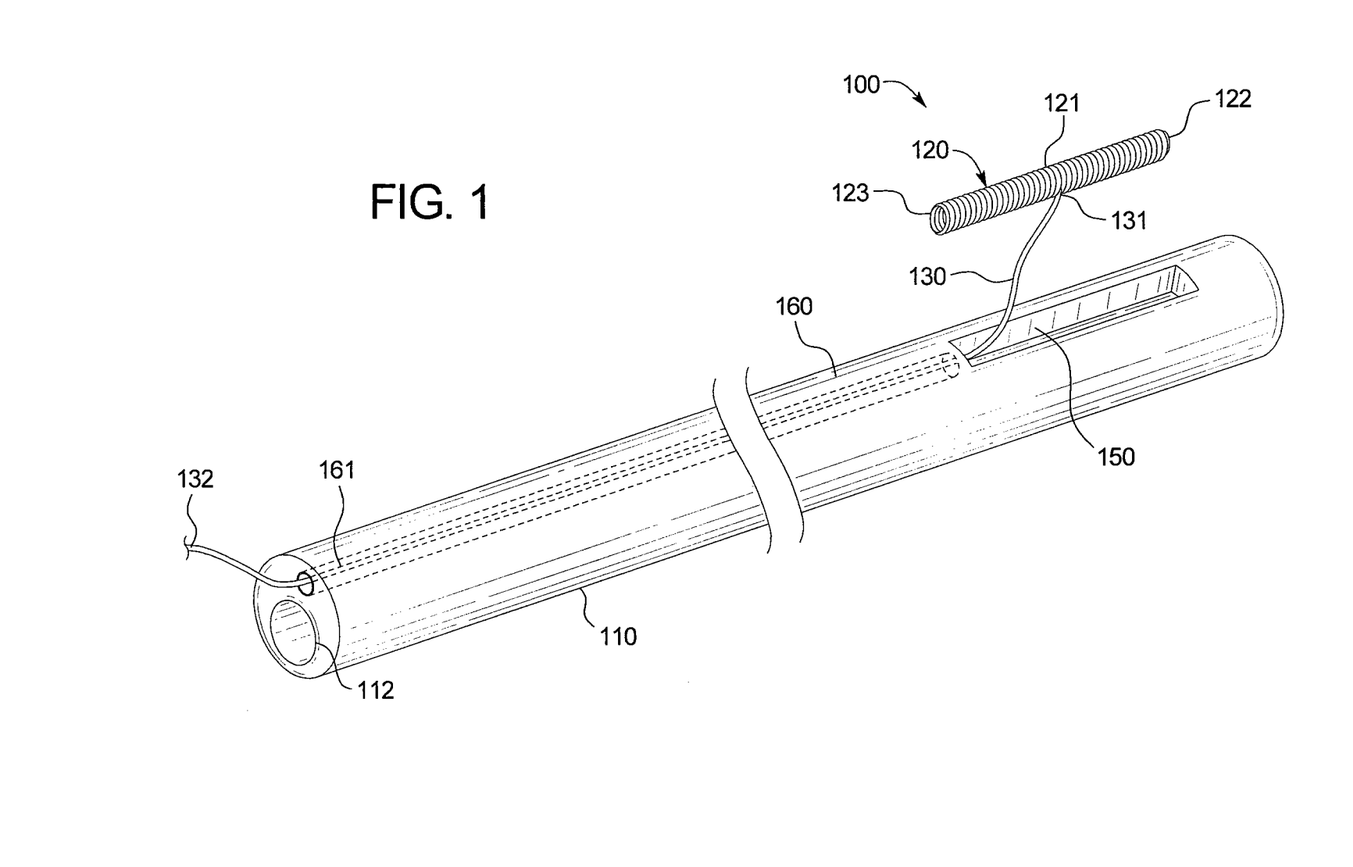
FIG. 1 is a perspective view of a gastrostomy feeding tube with an anchor assembly of the present invention.

FIG. 1 shows an example of a gastrostomy feeding tube 110 with a larger lumen 112 extending therethrough and an anchor assembly 100 disposed on a distal end thereof. The anchor assembly 100 comprises a pivotable anchor 120 and a filament 130. Generally speaking, the anchor assembly 100 enables the feeding tube 110 to be engaged against a body wall or secured within a body lumen.

During delivery of the feeding tube 110, the anchor 120 is configured to be longitudinally oriented within a recessed channel 150 of the feeding tube 110. The channel 150 preferably has a sufficient longitudinal length so that the entire anchor 120 is seated therewithin. The channel 150 preferably has a sufficient depth so that the anchor 120 is flush with the outer surface 160 of the feeding tube 110. Having the anchor 120 completely disposed within the recessed channel 150 and flush with the outer surface 160 may prevent inadvertent movement of the anchor 120 during delivery of the feeding tube 110 to the target site.

Filament 130 is shown connected to the body portion 121 of the anchor 120. The filament 130 has a first attached end 131 and a second unattached end 132. The first attached end 131 is affixed to the body portion 121 at a location between the first end 123 and the second end 122 of the anchor 120. Various means for affixing the first attached end 131 to the body portion 121 are contemplated, including wrapping the first attached end 131 around the anchor 120 or affixing the first attached end 131 to the anchor 120 by an adhesive. The second unattached end 132 extends outside of the patient. A significant region of the filament 130 between the second unattached end 132 and the first attached end 131 is disposed within lumen 161 of the feeding tube 110. Having a significant region of the wire 130 disposed within the lumen 161 protects the wire 130 from being exposed to an acidic gastric environment. Such concealment of the wire 130 also prevents the wire 130 from inadvertently catching on tissue or impediments during delivery and withdrawal of the feeding tube 110. Pulling on the second unattached end 132 causes the anchor 120 to be pulled out of the channel 150 and pivot from the longitudinal orientation (FIGS. 2A and 2B) to the substantially perpendicular orientation (FIG. 2c) in which the anchor 120 is oriented at about 90° relative to the notched surface 151 of the channel 150. The pivoting motion is shown by the rotational arrow in FIG. 2C. The anchor 120 may be secured and abutted against a visceral wall 400 (FIG. 4) to secure the feeding tube 110, as will be discussed in greater detail below.

The anchor 120 may be a cannula, cylindrical rod, coil, or cross bar. Other shapes for the anchor 120 are contemplated. The anchor 120 may be formed from any biocompatible material, including stainless steel. The Figures show that the anchor 120 comprises a helical coil formed from metallic material. The filament 130 may be constructed of common suture material as known in the art. For example, a polyester suture material such as 4-0 Tevdek® may be utilized. Other types of materials for the filament 130 are contemplated.

A lockable connector 300 (FIG. 3) may be affixed to the proximal end of the feeding tube 110. The lockable connector 300 maintains tension on the second unattached end 132 of the filament 130 to keep the anchor 120 in a substantially perpendicular orientation as shown in FIG. 2C. The lockable connector 300 includes a connector body 310 and a body passageway 360 through which the filament 130 extends. The body passageway 360 includes an external opening 370 so that the filament 130 proximally exits the connector body 310. The filament 130 terminates into the second unattached end 132, which is grasped as indicated by the arrow in FIG. 2C to pivot the anchor 110 from the longitudinal orientation to the perpendicular orientation. The lockable connector 300 also includes a lever 320. The lever 320 includes ends 321 and 322 and a cam surface 330 positioned about end 321. The lever 320 is pivotally interconnected about end 321 to a connector body 310 by a pivot pin.

Figure 3:
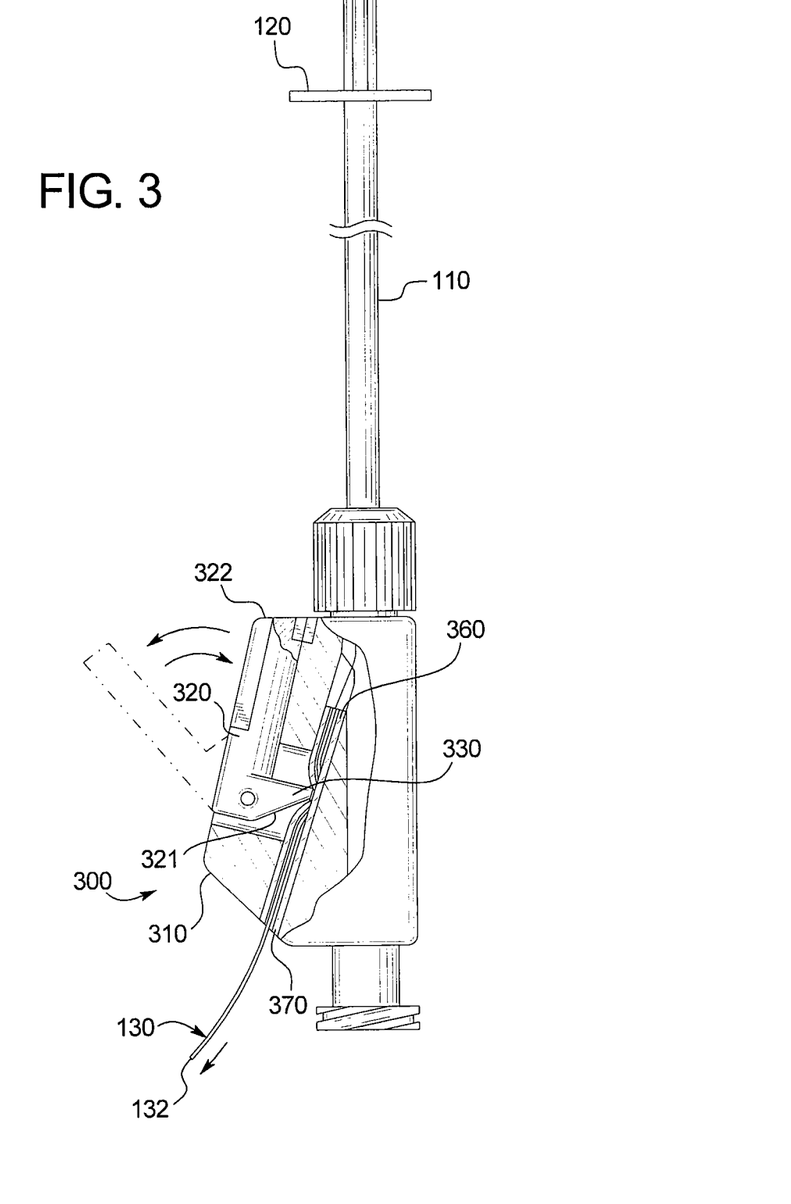
FIG. 3 is a perspective view of the feeding tube and anchor assembly of FIG. 1 with a lockable connector affixed to the proximal end of the feeding tube.

The filament 130 proximally extends through the lumen 161 of the feeding tube 110, the body passageway 360 of lockable connector 310, and thereafter proximally emerges from the external opening 370 as the second unattached end 132.

The lever 320 in FIG. 3 is shown in the engaged position. The cam surface 330 of the lever 320 is in a locked position compressing against filament 130 positioned through the body passageway 360. The engaged filament 130 maintains tension on the distal end of the filament 130, thereby keeping the anchor 110 in the perpendicular orientation. Other mechanisms for securing the proximal end of the filament 130 may be utilized. For example, the proximal end of the filament 130 may be merely tied off or knotted to maintain tension therein.

Variations of the anchor assembly 100 are contemplated. For example, multiple anchors 120 and corresponding filaments 130 may be disposed within the recessed channel 150 to increase the anchoring strength of the anchor assembly 100. Alternatively, multiple anchors 120 and corresponding filaments 130 may be oriented circumferentially along respective recessed channels 150.

Figure 4:
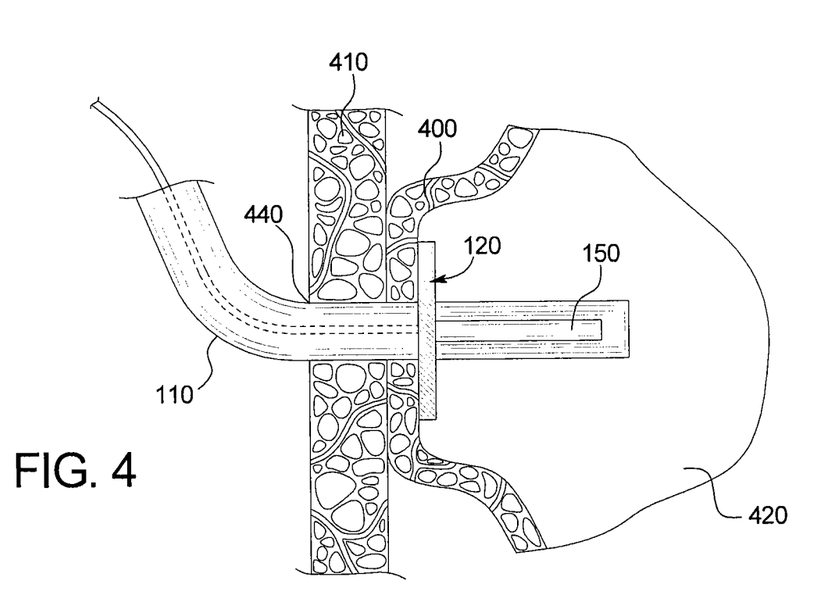
FIG. 4 shows a method of using the feeding tube and anchor assembly to anchor the feeding tube against a viscus wall.

One method of using the gastrostomy feeding tube 110 and anchor assembly 100 is shown in FIG. 4. FIG. 4 shows the gastrostomy feeding tube 110 in relation to a surgically created stoma 440 within the abdominal wall 410, wherein the anchor assembly 100 is in the deployment configuration at the target anchoring site.

Figure 2A:
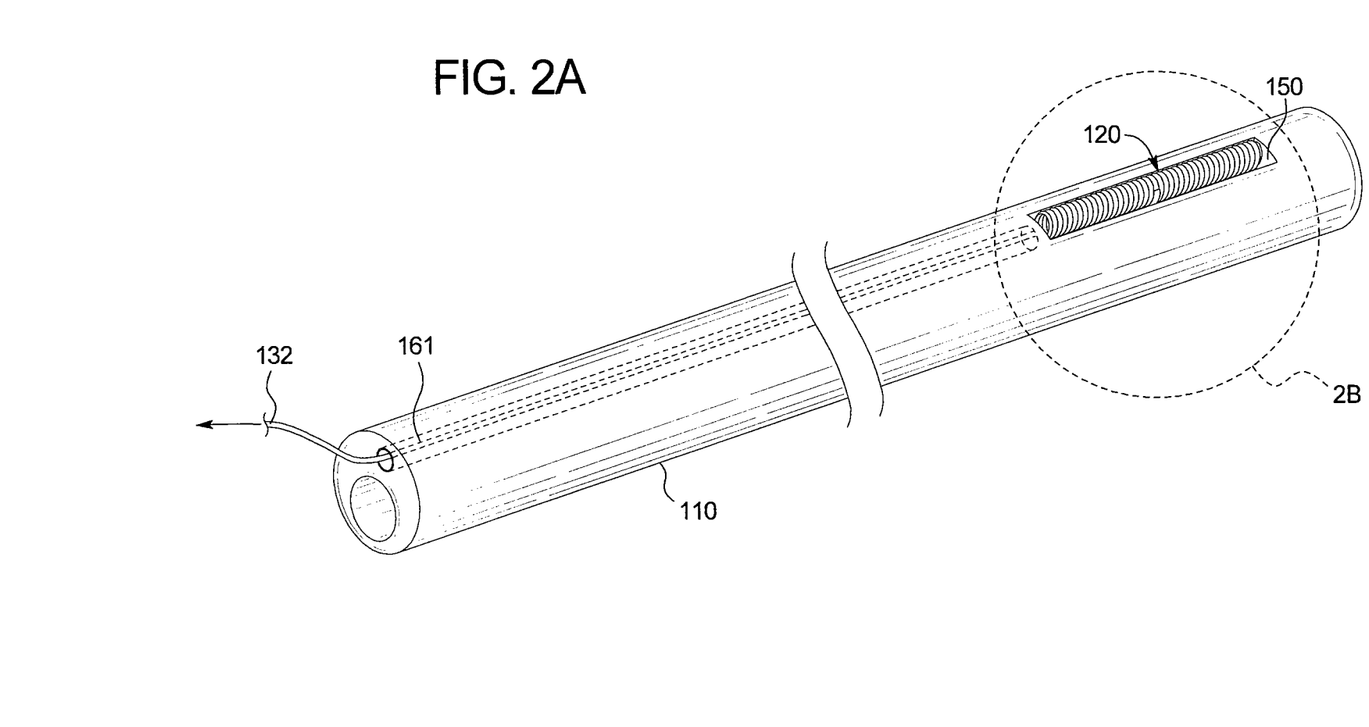
FIG. 2A is perspective view of FIG. 1 in which the anchor is seated within a recessed channel of the feeding tube.
Figure 2B:
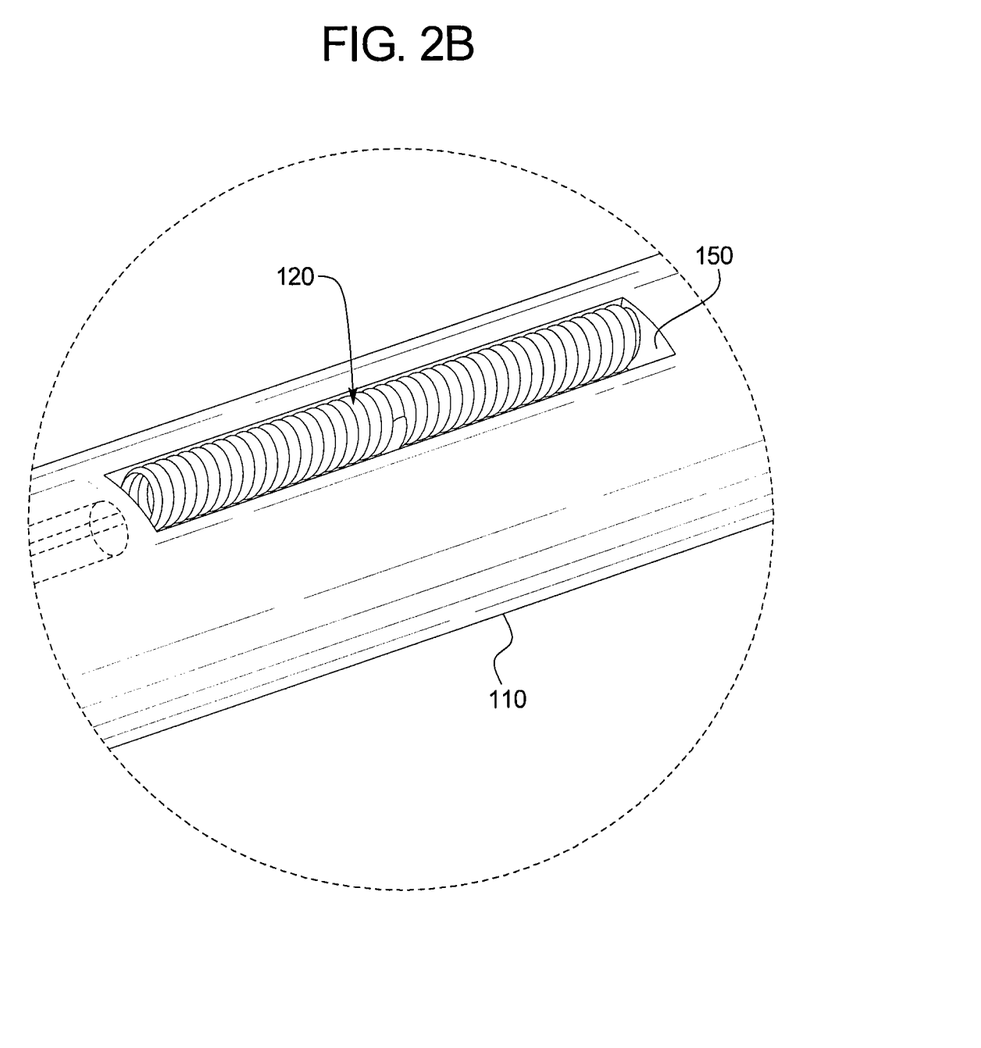
Figure 2C:
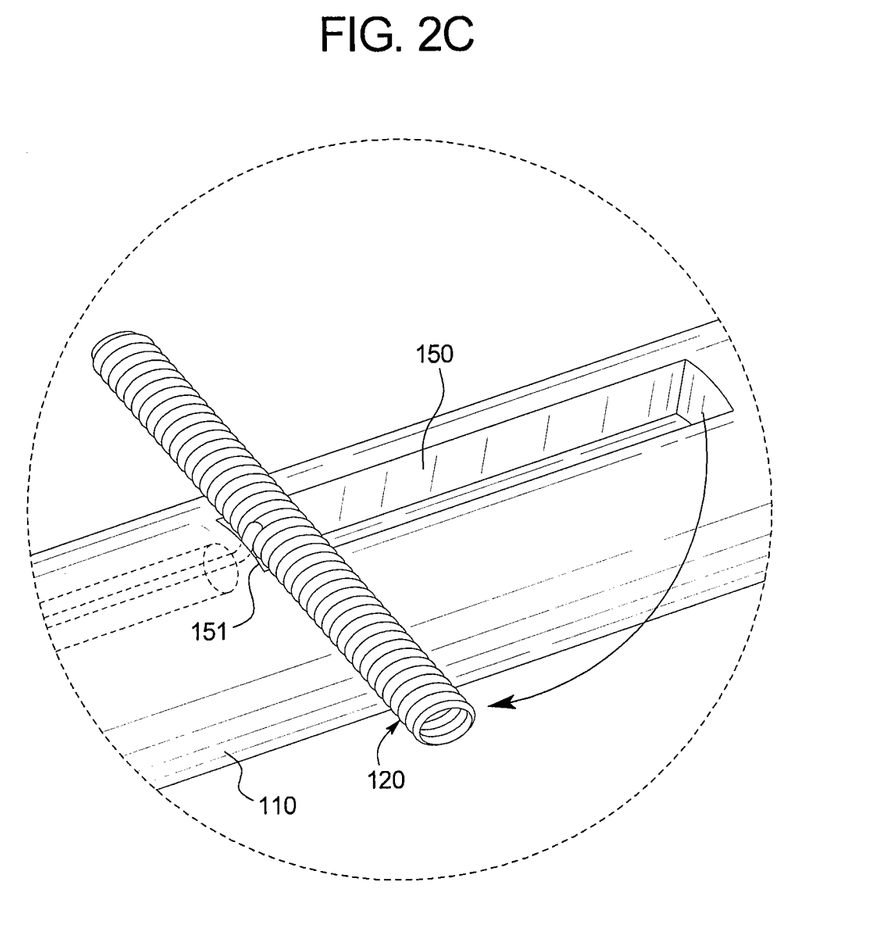
FIG. 2C is an expanded view of the anchor pivoted from the longitudinal to the perpendicular orientation.

Prior to delivery, the anchor assembly 100 is loaded within the slotted channel 150 as shown in FIGS. 2A and 2B. The distal end of the filament 130 is affixed to the anchor 120 at a location between the first attached end 123 and the second unattached end 122 of the anchor 120. In the example of FIGS. 2A and 2B, the filament 130 is affixed to about the midpoint of the anchor 120. Other locations of attachment of distal end of filament 130 between the first end 123 and the second end 122 of the anchor 120 are contemplated. The filament 130 is configured so that the region between the first attached end 123 and the second unattached end 122 extends through lumen 161 of the feeding tube 161. Configuring the wire 130 within lumen 161 may help to maintain and protect the integrity of the wire 130 after post-deployment compared to other filament anchors which expose the wire to the acidic gastric environment inherently present at the target site. Exposing the wire 130 to such an environment may also cause the wire 130 to inadvertently catch on body tissue.

Having loaded the anchor assembly 100 within channel 150 of the feeding tube 110, delivery to the target site may begin. During delivery, the anchor 120 is oriented within the channel 150 of the distal end of the feeding tube 100 (FIGS. 2A and 2B) to create a reduced lateral profile of the tube 110 and anchor assembly 100. Preferably, as shown in FIGS. 2A and 2B, the effective diameter of the anchor 120 is equal to or less than the depth of the channel 150, thereby substantially preventing inadvertent contact of the anchor with body tissue. Alternatively, a retractable outer sheath could be disposed over the feeding tube 100 and channel 150 and thereafter retracted to expose the slotted channel 150 when the feeding tube 100 has been delivered to the target site.

Still referring to FIG. 4, the distal end of the feeding tube 110 is pushed through the stoma 440 until the anchor 120 and channel 150 are completely disposed within the viscus lumen 420. If the optional retractable outer sheath is used, the practitioner performing the insertion can fixedly hold the outer sheath at the entrance of the stoma 440 and thereafter distally push the distal end of the feeding tube 110 relative to the stationary outer sheath through the stoma 440.

Having disposed the anchor 120 and channel 150 completely within the viscus lumen 420, the practitioner then pulls on the second unattached proximal end 132 of the filament 130 with a sufficient tensile force that causes the anchor 120 to pivot from the longitudinal orientation (FIG. 2B) to the perpendicular orientation (FIG. 2C). The pulling force is exerted on the second unattached end 132 of the filament 130 in the direction indicated by the arrow in FIG. 2A. The longitudinal length of the anchor 120 is greater than the opening of the stoma 440, thereby allowing anchor 120 in the perpendicular orientation to engage the internal viscus wall 400.

Having exerted the necessary tensile force on the second unattached end 132 of the filament 130, tension is maintained by engaging the proximal end of the wire 132 with a locking device, such as the lockable connector 300 of FIG. 3. Specifically, the lever 320 is pivoted into the engaged position. This causes the cam surface 330 of the lever 320 to be moved into a locked position to press against the filament 130 positioned through the body passageway 360. The engaged filament 130 maintains tension on the filament 130 to keep the anchor 110 in the perpendicular orientation (FIG. 2C).

At this juncture, the anchor 120 is firmly engaged against the interior viscus wall 400 by slightly withdrawing the feeding tube 110 in a proximal direction. As a result, the anchor 120 is positioned in perpendicular relation to the longitudinal axis of the stoma 440 as shown in FIG. 4. The feeding tube 110 may now serve as a pathway between the viscus lumen 420 (e.g., stomach) and the outside of the body.

Removal of the feeding tube 110 is achieved by disengaging the anchor 120 against the interior of the viscus wall 400. Disengagement may be achieved by pivotally moving the cam surface 330 of the lever 320 in a counterclockwise direction, as shown in phantom lines in FIG. 3. This causes the lever 320 to move from a locked position to an unlocked position in which the cam surface 330 does not press against the filament 130. The disengaged filament 130 ceases to maintain tension on the anchor 120. At this juncture, the feeding tube 110 may be withdrawn and the anchor 120 may simply pass through the patient.

Figure 5A:
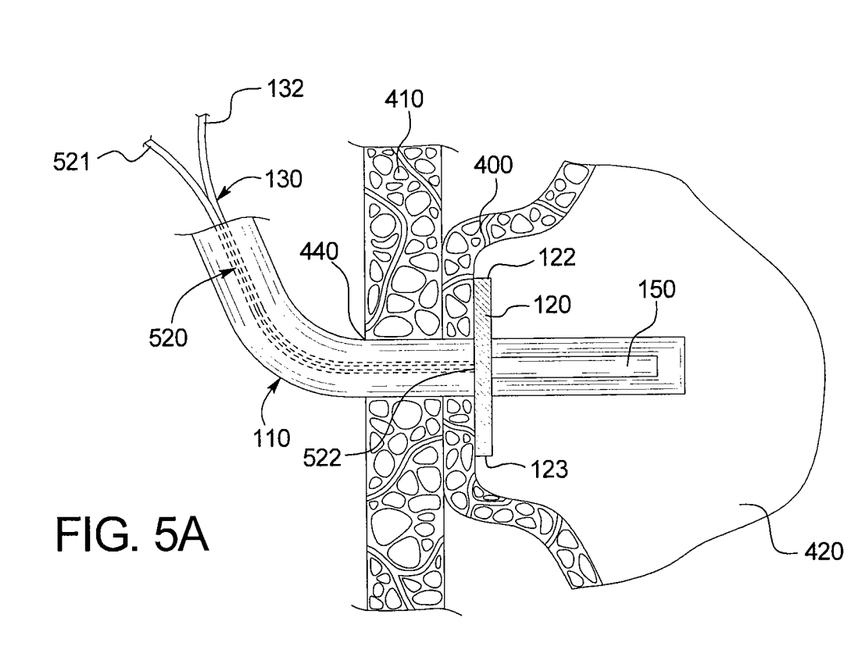
FIGS. 5A-5C shows another embodiment of an anchor assembly and a method of using the anchor assembly to anchor the feeding tube against a viscus wall.
Figure 5B:
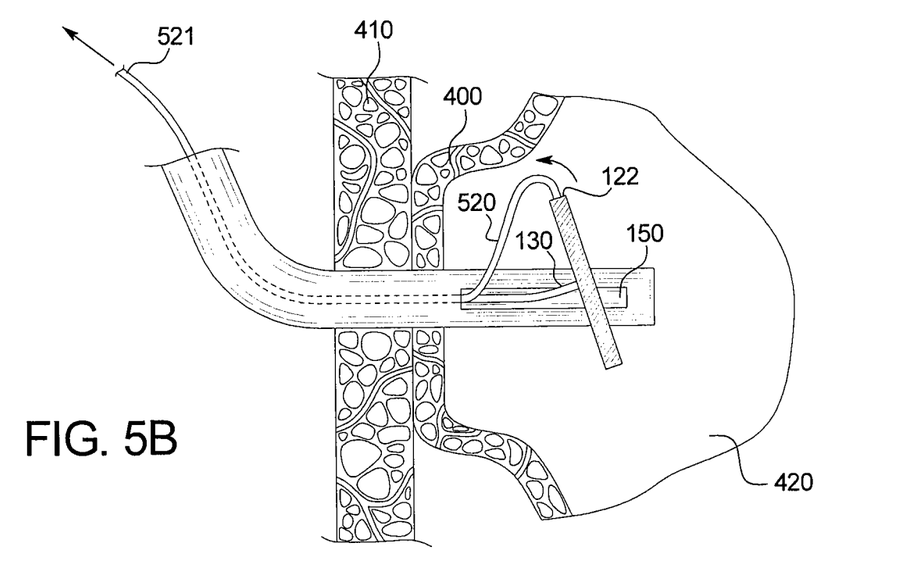
Figure 5C:
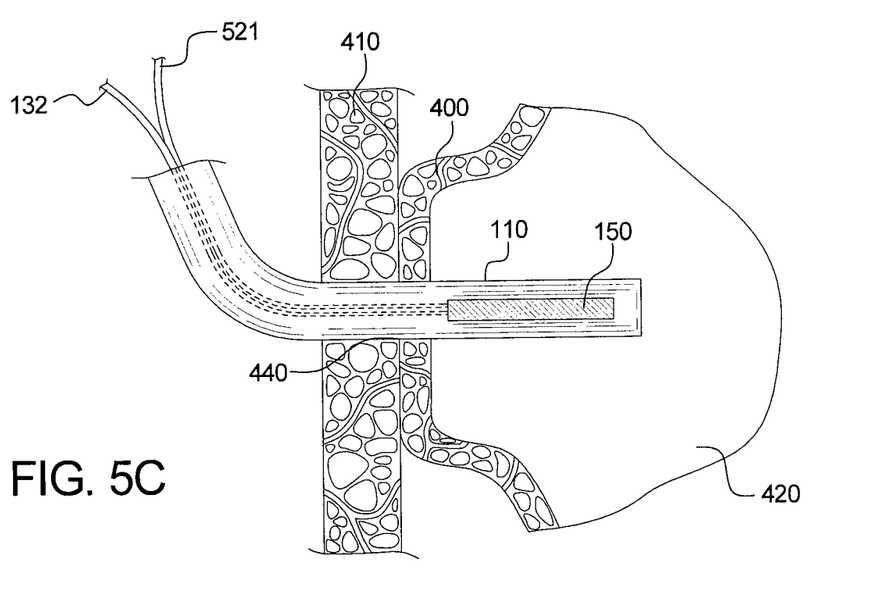

FIGS. 5A-5C show another embodiment in which the anchor 120 has a second filament 520 which may be used to pivot the anchor 120 from the perpendicular orientation to the longitudinal orientation. The distal end 522 of the second filament 520 may be affixed to either the first end 123 or the second end 122. In the example of FIG. 5A, the distal end 522 is affixed to the first end 123. Similar to second unattached end 132 of filament 130, the proximal free end 521 of 520 emerges from the proximal end of the feeding tube 110. The wire 520 between the proximal free end 521 and the distal end 522 is disposed within a lumen of the feeding tube 110. The wire 520 may be disposed in a lumen separate from wire 130. Alternatively, the wires 130 and 520 may be disposed in a common lumen.

After the feeding tube 110 is no longer needed, the anchor 120 may be realigned with the longitudinal axis of the feeding tube 110 and reinserted into recessed channel 150 so that the anchor 120 and feeding tube 110 may be withdrawn from the viscus lumen 420. The longitudinal realignment of the anchor 120 may be achieved by removing tension from filament 130. If the lockable connector 300 is utilized, the release of tension may be achieved by disengaging the lever 320 of lockable connector 310 (FIG. 3) so that the cam surface 330 does not compress against the filament 130. Alternatively, if a practitioner is holding under tension the second unattached proximal end 132 of filament 130, the physician may release his grip from the proximal end 132 to release the tension.

Having released tension on wire 130, the practitioner holds the second unattached proximal end 132 of filament 130 close to the proximal end of feeding tube 161 and thereafter pushes the proximal end 132. This pushing will distally advance the anchor 120 along channel 150. The proximal end 132 is pushed along channel 150 a sufficient amount to provide space for the pivoting of the anchor 120 from the perpendicular orientation to the longitudinal orientation. At this juncture, FIG. 5B shows that the proximal free end 521 is pulled in the direction of the arrow to cause anchor 120 to pivot counterclockwise about second end 122. When anchor 120 pivots into a substantially longitudinal orientation, the anchor 120 may be reconfigured within recessed channel 150 (FIG. 5C).

An alternative method for longitudinally realigning the anchor 120 is as follows. The feeding tube 110 may be advanced a sufficient distance within viscus lumen 420 so as to provide space for anchor 120 to pivot from the perpendicular to the longitudinal orientation. After distally advancing feeding tube 110 within viscus lumen 420, the tension on filament 130 is removed. Having released tension on filament 130, the practitioner pulls on proximal free end 521 of filament 520 to cause the anchor 120 to pivot from the perpendicular orientation to a longitudinal orientation (FIG. 5B) and reconfigure within recessed channel 150 (FIG. 5C).

Either method may be used to longitudinally realign the anchor 120 so that the anchor assembly 100 and feeding tube 120 may be withdrawn from the viscus lumen 420.

Although the Figures are directed to a gastrostomy feeding it should be understood that the anchor assembly 100 may be incorporated into other medical devices and may be utilized in a variety of locations within the body. As an example, the anchor assembly 100 may be incorporated into a drainage catheter for percutaneously draining fluid from the bladder of a patient. The anchor assembly 100 on the drainage catheter may fixate the catheter within a biliary duct.

The above figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

The invention claimed is:

1. A medical device with an anchor assembly, comprising:
   an elongate member having a proximal end and a distal end, the elongate member comprising a longitudinally oriented first channel comprising a length that is recessed and open to a radial outer surface of the elongate member near the distal end;
   a smaller lumen extending from the first channel, through the elongate member, and communicating with an exterior opening configured to be disposed outside of a patient;
   a pivotable anchor comprising an entire length that is removably disposed within the first channel, the pivotable anchor comprising a proximal end adjacent a distal opening of the smaller lumen when the pivotable anchor is disposed within the first channel, the proximal end being larger in size than the distal opening of the smaller lumen such that the pivotable anchor does not extend into the smaller lumen, the pivotable anchor being movable from the first channel to a perpendicular orientation outside the first channel and adjacent to the elongate member and the distal opening of the smaller lumen, the distal end of the elongate member thereby being fixed a predetermined distance from the pivotable anchor when the pivotable anchor is in the perpendicular orientation and adjacent the elongate member and the distal opening of the smaller lumen;
   a larger lumen extending from a separate exterior opening configured to be disposed outside of the patient, through the elongate member, and opening distal from the distal opening of the smaller lumen;
   a biocompatible filament having a first attached end affixed to the anchor and a second unattached proximal end configured to be disposed outside of the patient, the filament proximally extending from the first attached end to the second unattached end within the smaller lumen of the elongate member;
   wherein the anchor is configured to pivot from a longitudinal orientation within the first channel to the perpendicular orientation outside the first channel upon application of a tensile force to the second unattached proximal end of the filament, the anchor in the perpendicular orientation being configured to engage against a body wall to inhibit movement of the elongate member thereto.

2. The medical device of claim 1, further comprising a lockable connector operably connected to the proximal end of the elongate member, the lockable connector comprising a pivotal lever having a cam surface and movable between a locked position and an unlocked position, wherein the cam surface engages the filament when in the locked position.

3. The medical device of claim 2, wherein the cam surface when in the locked position grips the filament between the cam surface and an opposing surface of the connector.

4. The medical device of claim 2, the lockable connector further comprising a first body passageway communicating with the smaller lumen of the elongate member, the first body passageway having the exterior opening for passage of the filament therethrough.

5. The medical device of claim 1, further comprising a plurality of anchors.

6. The medical device of claim 5, wherein each of the plurality of anchors is disposed within a corresponding channel.

7. The medical device of claim 6, wherein the plurality of anchors are circumferentially disposed about the distal end of the elongate member.

8. The medical device of claim 1, wherein the anchor comprises a helical coil formed from metallic material.

9. The medical device of claim 1, wherein the first channel comprises a longitudinal length about equal to a longitudinal length of the anchor.

10. The medical device of claim 1, wherein the first channel comprises a depth at least equal to an effective diameter of the anchor.

11. A medical device with an anchor assembly, comprising:
    an elongate device having a proximal end and a distal end, the elongate device comprising a longitudinally oriented first channel comprising a length that is recessed and open to a radial outer surface of the elongate device near the distal end thereof, wherein the channel is sufficiently sized for an anchor to be seated therewithin along the outer surface of the elongate device;
    a smaller lumen extending from the first channel, through the elongate member, and communicating with an exterior opening configured to be disposed outside of a patient;
    a pivotable anchor comprising an entire length that is removably disposed within the first channel, the anchor comprising a first end and a second end, and an effective diameter less than or equal to a depth of the channel, the first end being adjacent a distal opening of the smaller lumen when the pivotable anchor is disposed within the first channel, the first end being larger in size than the distal opening of the smaller lumen such that the pivotable anchor does not extend into the smaller lumen, the anchor being movable from the first channel to a perpendicular orientation outside the first channel and adjacent to the elongate device and the distal opening of the smaller lumen, the distal end of the elongate device thereby being fixed a predetermined distance from the pivotable anchor when the pivotable anchor is in the perpendicular orientation and adjacent the elongate device and the distal opening of the smaller lumen;
    a larger lumen extending from a separate exterior opening configured to be disposed outside of the patient, through the elongate device, and opening distal from the distal opening of the smaller lumen;
    a first tension member having a first attached end affixed to the anchor, the first attached end being affixed to the anchor at about a midpoint of the anchor, the first tension member further comprising a second unattached proximal end configured to be located outside of the patient, the first tension member proximally extending from the first attached end to the second unattached end within the smaller lumen of the elongate device;
    a lockable connector operably connected to the proximal end of the elongate device, the lockable connector comprising a pivotal lever having a cam surface and movable between a locked position and an unlocked position, wherein the cam surface engages the tension member when in the locked position; and
    wherein the anchor is configured to pivot from a longitudinal orientation within the first channel to the perpendicular orientation outside the first channel upon application of a tensile force to the second unattached proximal end of the tension member, the anchor in the perpendicular orientation being configured to engage against a body wall to inhibit movement of the elongate device thereto.

12. The medical device of claim 11, further comprising a second tension member having a third attached end and a fourth unattached end configured to be located outside of the patient, the third attached end being attached to one of the first and the second ends of the anchor.

13. The medical device of claim 12, wherein application of a tensile force to the fourth unattached end causes the anchor to move from the perpendicular to the longitudinal orientation.

14. The medical device of claim 12, wherein the second tension member proximally extends from the third attached end to the fourth unattached end within another lumen of the elongate device.

15. A method of anchoring an elongate member within a body lumen, comprising the steps of:
(a) providing an anchor assembly comprising:
  (i) an anchor;
  (ii) a biocompatible filament having a first attached end affixed to the anchor and a second unattached proximal end,
(b) loading an entire length of the anchor within a channel, the channel comprising a length that is recessed and open to a radial outer surface of the elongate member, wherein the anchor is longitudinally oriented within the channel;
(c) configuring the second unattached proximal end through a smaller lumen of the elongate member, the second unattached proximal end extending through the smaller lumen of the elongate member and emerging from the smaller lumen as a free end outside of a body of a patient, wherein the smaller lumen extends from the channel and a proximal end of the anchor is disposed adjacent a distal opening of the smaller lumen when the anchor is disposed within the channel, the proximal end being larger in size than the distal opening of the smaller lumen such that the anchor does not extend into the smaller lumen;
(d) positioning the elongate member with the anchor assembly at a target body site;
(e) pulling the free end with a sufficient force;
(f) pivoting the anchor from the longitudinal orientation to a perpendicular orientation relative to the elongate member outside the channel and adjacent to the elongate member and the distal opening of the smaller lumen, a distal end of the elongate member thereby being fixed a predetermined distance from the anchor when the anchor is in the perpendicular orientation and adjacent the elongate member and the distal opening of the smaller lumen; and
(g) engaging the anchor against a body wall of the target body site so as to secure the elongate member relative thereto, a larger lumen extending from an exterior opening disposed outside of the patient, through the elongate member, and opening into the patient distal from the distal opening of the smaller lumen.

16. The method of claim 15, further comprising the step of:
(h) maintaining tension on the filament by locking the free end into a lockable connector.

17. The method of claim 16, further comprising the step of:
(i) disengaging the anchor from the body wall; and
(j) withdrawing the elongate member.

18. The method of claim 17 wherein step (i) further comprises longitudinally realigning the anchor into the channel.

* * * * *